(12) United States Patent
Liao et al.

(10) Patent No.: US 9,075,065 B2
(45) Date of Patent: Jul. 7, 2015

(54) PROSTATE CANCER BIOMARKER

(75) Inventors: Zhiming Liao, Ventura, CA (US); Uffe Lovborg, Tucson, AZ (US)

(73) Assignee: Dako Denmark A/S, Glostrup (DK)

( * ) Notice: Subject to any disclaimer, the term of this patent is extended or adjusted under 35 U.S.C. 154(b) by 294 days.

(21) Appl. No.: 13/063,320

(22) PCT Filed: Sep. 10, 2009

(86) PCT No.: PCT/DK2009/000202
§ 371 (c)(1),
(2), (4) Date: May 24, 2011

(87) PCT Pub. No.: WO2010/028646
PCT Pub. Date: Mar. 18, 2010

(65) Prior Publication Data
US 2011/0236910 A1      Sep. 29, 2011

Related U.S. Application Data

(60) Provisional application No. 61/096,389, filed on Sep. 12, 2008.

(51) Int. Cl.
*C12Q 1/00* (2006.01)
*G01N 33/53* (2006.01)
*G01N 33/574* (2006.01)

(52) U.S. Cl.
CPC .................. *G01N 33/57434* (2013.01)

(58) Field of Classification Search
None
See application file for complete search history.

(56) References Cited

FOREIGN PATENT DOCUMENTS

| EP | 0 368 684 B1 | 3/1994 |
|---|---|---|
| EP | 0 589 877 B1 | 11/1996 |
| EP | 0 436 597 B1 | 4/1997 |
| EP | 0 623 679 B1 | 6/2003 |

OTHER PUBLICATIONS

Peterson et al, J Cell Science 102:581-600 1992.*
Bismar et al AJCP 121:557-563, 2004.*
Miller et al proteomics 3:56-63, 2003, IDS filed Jun. 5, 2013.*
Herawi et al, Human Pathology 38: 72-78, 2007.*
Bizmar et al., "Expression of β-Catenin in Prostatic Adenocarcinomas" *Anatomic Pathology* 121:557-563 (2004).
European Search Report for EP 09776198.5, dated Aug. 5, 2011.
Goldstein, "Immunophenotypic Characterization of 225 Prostate Adenocarcinomas with Intermediate or High Gleason Scores" *Am. J. Clin. Pathol.* 117(3):471-477 (Mar. 2002).
Kang et al., "Linkage of recognition and replication functions by assembling combinatorial antibody Fab libraries along phage surfaces" *Proc. Natl. Acad. Sci. USA* 88:4363-4366 (May 1991).
Kohler and Milstein, "Continuous cultures of fused cells secreting antibody of predefined specificity" *Nature* 256:495-497 (Aug. 7, 1975).
Marks et al., "By-passing Immunization: Building High Affinity Human Antibodies by Chain Shuffling" *Bio/Technol.* 10:779-783 (Jul. 1992).
McCafferty et al., "Phage antibodies: filamentous phage displaying antibody variable domains" *Nature* 348:552-554 (1990).
Paner et al., "Best Practice in Diagnostic Immunohistochemistry: Prostate Carcinoma and Its Mimics in Needle Core Biopsies" *Arch. Pathol. Lab. Med.* 132(9):1388-1396 (Sep. 2008).
Waterhouse et al., "Combinatorial infection and in vivo recombination: a strategy for making large phage antibody repertoires" *Nucl. Acid Res.* 21(9):2265-2266 (1993).
Hameed et al., "Immunohistochemistry in diagnostic surgical pathology of the prostate," *Seminars in Diagnostic Pathology.* 22:88-104 (2005).
International Search Report for PCT/DK2009/000202 mailed Jan. 25, 2010.
Miller et al., "Antibody microarray profiling of human prostate cancer sera: antibody screening and identification of potential biomarkers," *Proteomics* 3:56-63 (2003).
Musser et al., "CDX2 and Villin are useful markers for metastatic colorectal cancer," 3rd International Congress of Pathology; Barcelona, Spain; May 17-22, 2008; *Virchows Archiv* 452:S203-S204; Abstract P-376 (2008).
Miller et al., "Antibody microarray profiling of human prostate cancer sera: Antibody screening and identification of potential biomarkers", *Proteomics* 3: 56-63 (2003).
Hameed et al., "Immunohistochemistry in diagnostic surgical pathology of the prostate", *Seminars in Diagnostic Pathology* 22: 88-104 (2005).

* cited by examiner

*Primary Examiner* — Lei Yao
(74) *Attorney, Agent, or Firm* — Finnegan, Henderson, Farabow, Garrett & Dunner, L.L.P.

(57) ABSTRACT

The present invention relates to the field of prostate cancer. Particularly the invention relates to villin as a novel prostate biomarker. The invention further relates to compositions comprising anti-villin antibodies and use of these compositions for an improved detection of prostate cancer in a subject.

6 Claims, 1 Drawing Sheet

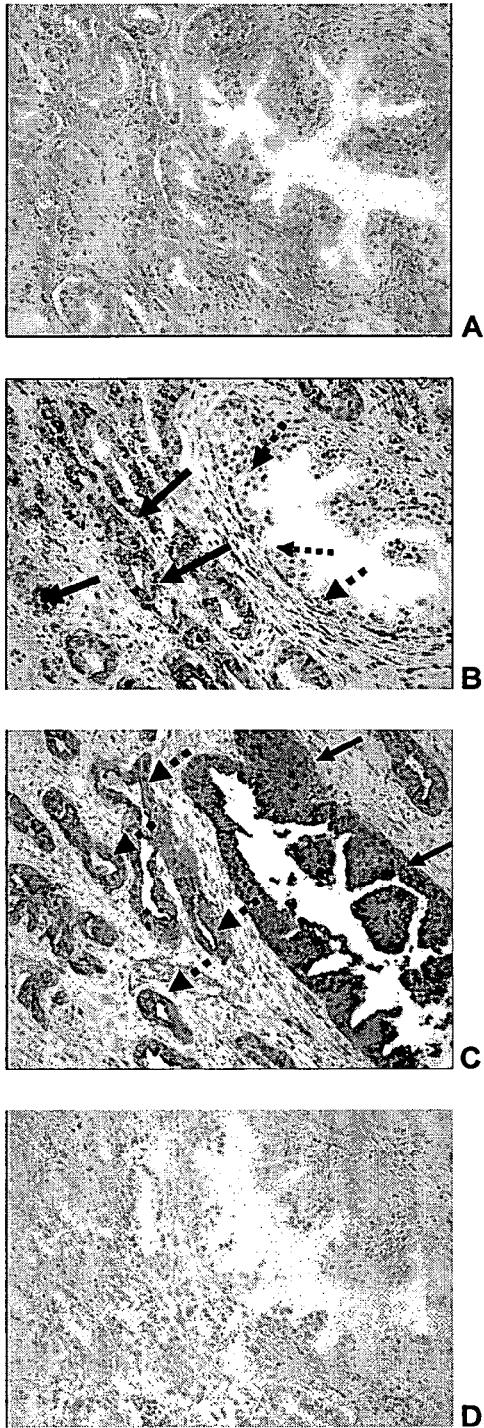

IHC staining of villin, PSA, and CDX-2 in a prostate cancer sample.

A. Typical morphology of prostate adenocarcinoma is shown in H&E staining.

B. Villin is positive in all cancer cells but negative in the hyperplastic gland cells C. PSA is positive in all cancer cells and the hyperplastic gland cells.

D. CDX-2 is negative in both cancer and normal cells of the prostate.

↙ cancer cells

↙ hyperplastic cells

PROSTATE CANCER BIOMARKER

CROSS-REFERENCE TO RELATED APPLICATIONS

This application is a U.S. national stage entry under 35 U.S.C. §371 of International Application Number PCT/DK2009/000202, filed Sep. 10, 2009, which claims the benefit of U.S. Provisional Application Number 61/096,389, filed Sep. 12, 2008, both of which are incorporated herein by reference.

TECHNICAL FIELD

The present invention relates to the filed of prostate cancer. Particularly, the invention relates to a novel prostate biomarker, villin, and compositions comprising villin for an improved detection of prostate cancer.

BACKGROUND OF THE INVENTION

Prostate carcinoma is the most common type of cancer in men. Early detection of prostate cancer when the cancer is confined to the prostate gland has the best chance of cure through radical prostatectomy (surgery). Prostate specific antigen (PSA) is considered as an effective tumor marker and is for most intents and purposes organ specific. However, PSA is not cancer specific. There is a considerable overlap in PSA concentrations in men with prostate cancer and men with benign prostatic diseases. PSA could not differentiate men with organ confined prostate cancer (who would benefit from surgery) from those men with non-organ confined prostate cancer (who would not benefit from surgery). Therefore, PSA is not effective as prostate cancer biomarker in selecting subjects for radical prostatectomy, and identification of new prostate cancer biomarker is needed for the better diagnosis, characterization, and treatment of the prostate cancer.

Villin is the major protein associated with actin of the intestinal microvillus. Its presence has been demonstrated in the brush border of digestive system (esophagus, intestinal, biliary system, and pancreas) and kidney. It has been used as biomarker for neuroendocrine tumors of gastrointestinal tract and lung, and the differential diagnosis between metastatic colonic carcinoma and carcinoma from other organs in human.

A study aimed to the identification of potential biomarkers in prostate cancer serum by protein profiling using antibody microarrays has demonstrated that the level of villin differs significantly between serum samples of prostate cancer subjects and control (Miller J C, Zhou H, Kwekel J, Cavallo R, Burke J, Butler E B, Teh B S, Haab B B: Antibody microarray profiling of human prostate cancer sera: antibody screening and identification of potential biomarkers, Proteomics 2003, 3:56-63). However, for now there has not been demonstrated villin also presents in tissues of prostate and prostate cancer (Goldstein, N S. Immunophenotypic characterization of 225 prostate adenocarcinomas with intermediate or high Gleason scores. Am J Clin Pathol. 2002 March; 117(3):471-7; Hameed, O., Humphrey, P A. Immunohistochemistry in diagnostic surgical pathology of the prostate. Semin Diagn Pathol. 2005 February; 22(1):88-104; Paner G P, Luthringer D J, Amin M B. Best practice in diagnostic immunohistochemistry: prostate carcinoma and its mimics in needle core biopsies. Arch Pathol Lab Med. 2008 September; 132(9): 1388-96).

SUMMARY OF THE INVENTION

The present invention provides methods and kits for in vitro determining the presence of prostate cancer cells in a subject. The methods of the invention comprise immunochemical determining of the level of expression of villin in samples of solid body tissues and tumors, i.e. exculing blood samples, obtained from a subject in vitro, in particular the invention relates to determining of the level of expression of villin in samples of prostate tissue and prostate tumors. The determining the level of expression of villin in the latter samples provides information that diagnosticians can correlate with a probable diagnosis of cancer or the negative diagnosis (e.g., normal or cancer-free). The aspects of the invention also include a method of selecting subjects for a particular treatment such as a radical prostatectomy or non-invasive therapeutic treatment, wherein the selection is based on in vitro immunochemical determining of the level of expression of villin in samples of prostate obtained from said subjects.

DESCRIPTION OF FIGURES

FIG. 1 demonstrates the results of immunohistochemical staining (IHC) of prostate cancer tissue samples with villin, prostate specific antigen (PSA) and CDX-2 specific antibodies.

DETAILED DESCRIPTION OF THE INVENTION

The present invention relates to an unexpected finding that prostate cancer cells express villin.

Accordingly, a first aspect of the invention relates to a method for detecting a prostate cancer in a subject, comprising in vitro immunochemically determining the presence of villin in a sample of prostate or another solid body tissue or tumor obtained from said subject. "Subject" as used herein means human male individual that may be a healthy, i.e. normal, or sick, i.e. a patient, male individual.

"Prostate cancer" refers to a neoplasm, e.g., malignant neoplasm, of the prostate within a given subject, wherein the neoplasm is of epithelial origin. The term "prostate cancer", when used without qualification, includes both localized and metastasized prostate cancer. The term "prostate cancer" can be qualified by the terms "localized" or "metastasized" to differentiate between different types of tumor, where a "localized" refers to the original mother tumour, and the metastasized to the tumours that has spread from the original mother tumour. In one embodiment the invention relates to detection of metastasized cancer cells of prostate cancer origin in samples of human body tissues and tumors other than prostate.

There are many types of prostate cancer and the condition is often present in many different parts of the prostate. The precursor to prostate cancer is known as prostatic intraepithelial neoplasia, this is also found in many different locations within the prostate. Although there are many different kinds of prostate cancer the vast majority (around 95%) are of the type known as adenocarcinoma. As this is the most wide spread from it has become synonymous with the term prostrate cancer. Accordingly, in one embodiment the invention relates to determining the presence of prostate adenocarcinoma in a subject.

In another embodiment the invention also relates to determining the presence of prostate small cell carcinoma in a subject. This kind of cancer is made up of small round cells, and typically forms at nerve cells. Small cell carcinoma is very aggressive in nature and as it does not lead to an increase in prostate specific antigens it can be somewhat harder to detect than adenocarcinoma; this usually means that it has reached an advanced form upon detection In another embodiment the invention also relates to determining the presence of prostate squamous cell carcinoma in a subject. This is a non glandular cancer, like small cell carcinoma there is no increase in prostate specific antigens when this is present. Squamous cell carcinoma is very aggressive in nature.

The invention also concerns detection of other, more rare, forms of prostate cancer; these include sarcomas and transitional cell carcinoma; the latter rarely develops in the prostate but derives from primary tumours present in the bladder or urethra.

The invention relates to human villin protein, a calcium-regulated actin-binding protein of molecular weight 95,000, which is encoded by the villin gene (VIL) having location 2q35-q36. Villin is known as a protein that specifically expressed in simple epithelia of some tissues of the gastrointestinal and urogenital tracts.

Determining the level of expression of villin in tissue or tumor samples is according to the invention performed immunochemically, i.e. utilizing an anti-villin antibody.

"Detection", "detect", "detecting" used herein interchangeably with the term "determining", "determination" and includes qualitative and/or quantitative detection (measuring levels) with or without reference to a control, and further refers to the identification of the presence, absence, or quantity of a given protein, specifically villin. "Level of expression" means the presence of villin in an analysed sample from at 0, i.e. the protein is not expressed, to any detectable amount.

According to the invention, the presence of villin in a tissue sample obtained from a subject is indicative of that tissue sample comprise prostate cancer cells; the absence of villin in the sample indicates that the sample is free of prostate cancer cells.

The term "antibody", as used herein, designates an immunoglobulin or a part thereof, and includes any polypeptide comprising an antigen-binding site regardless of the source, method of production, and other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can still bind antigen, for example, an Fab, $F(ab')_2$, Fv, scFv. The origin of the antibody is defined by the genomic sequence irrespective of the method of production.

Immunological determination of villin may be performed by utilizing any suitable method known in the art for such determination, e.g. immunoblotting, ELISA, immunohistochemistry (IHC). In one embodiment the expression of villin is determined by IHC. In another embodiment the expression of villin is determined by immunoblotting or ELISA, e.g. in a cell-free sample of a solid tissue, e.g. a tissue homogenate, cell supernatant or protein fraction of said homogenate or supernatant.

Anti-villin antibodies may be produced according to the well-known in the art procedures or purchased from antibody manufactures. Any commercially available antibodies capable of specifically binding to villin of the invention in the conditions of a chosen detection assay may be used for the purposes of the invention, for example, Mouse Anti-Villin Monoclonal Antibody, Clone 12 from Abcam, or Mouse Anti-Villin Monoclonal Antibody, Unconjugated, Clone 1D2C3 from BIOCARE MEDICAL, etc. In one embodiment, the invention relates to Mouse Anti-Villin Monoclonal Antibody, Clone 1D2 C3 from DAKO.

Antibodies may be polyclonal, monoclonal, recombinant, or villin-binding fragments thereof.

Various techniques for producing antibodies have been described, see, e.g., Kohler and Milstein, (1975) Nature 256: 495; Harlow and Lane, Antibodies: a Laboratory Manual, (1988) Cold Spring Harbor Press, Cold Spring Harbor, N.Y.) incorporated herein by reference. Techniques for the preparation of recombinant antibody molecules is described in the above references and also in, for example, EP 0623679; EP 0368684; and EP 0436597. Antibodies may be produced recombinantly or synthetically. Nucleic acids encoding antibodies may be isolated from a cDNA library. Nucleic acids encoding antibodies may be isolated from a phage library (see e.g. McCafferty et al. 1990, Nature 348:552, Kang et al. 1991, Proc. Natl. Acad. Sci. USA 88:4363; EP 0 589 877 B1). Nucleic acids encoding antibodies can be obtained by gene shuffling of known sequences (Mark et al. 1992, Bio/Technol. 10:779). Nucleic acids encoding antibodies can be isolated by in vivo recombination (Waterhouse et al. 1993, Nucl. Acid Res. 21:2265).

In one embodiment the antibodies may be derivatized, e.g conjugated with a label, i.e. a detectable substance or hapten, and/or a polymer, e.g. a dextran polymer. Such deriviatized antibodies are also commercially available, e.g. form the producers mentioned above. Otherwise, the antibodies may be manipulated and conjugated with a label or polymer according to the procedures well-known in the art (see e.g. Harlow E. and Lane D., Using Antibodies: A Laboratory Manual. (1999) Cold Spring Harbor Press, Cold Spring Harbor, N.Y.).

Many products which are suitable for detection of antigens by IHC are also commercially available, e.g. Envision™+ (Dako), Powervision® (Immunovision), NBA™ kit (Zymed Laboratories Inc.), HistoFine® (Nichirei Corp.).

A sample of a solid body tissue or tumor, e.g. prostate, may be a fresh biopsy sample. It may also be a sample archived tissue, e.g. formalin fixed and paraffin embedded tissue. The term "sample" encompasses a variety of sample types obtained from subjects having or not having prostate cancer. Exemplary samples useful in the disclosed methods include but are not limited to solid tissue samples such as a biopsy specimen or tissue cultures or cells derived there from, and the progeny thereof, cell supernatants, cell lysates etc.

Particular, but non-limiting, examples are prostate biopsies and/or prostatectomy tissues, or prostate cell samples (such as can be collected by prostate massage, in the urine, or in fine needle aspirates). As mentioned, samples may be fresh or processed post-collection (e.g., for archiving purposes). In some examples, processed samples may be fixed (e.g., formalin-fixed) and/or wax- (e.g., paraffin-) embedded. Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, Histotechology: A Self-Instructional Text, Chicago: ASCP Press, 1997). In some examples, the sample (or a fraction thereof) is present on a solid support.

Solid supports useful in a disclosed method need only bear the biological sample and, optionally, but advantageously, permit convenient detection of the proteins of interest in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE®; chips.

A tissue sample may be obtained from a subject according to the standard procedures known to the skilled in the art.

Thus, in one embodiment the invention relates to a method of diagnosing a primary prostate cancer in a subject, comprising in vitro immunochemically determining expression of villin in a sample of prostate tissue obtained from said subject. In another embodiment the invention relates to a method of diagnosing a metastatic cancer of prostate origin in a subject, comprising in vitro immunochemically determining expression of villin in a sample of a solid tissue or tumor obtained from said subject.

Another aspect of the invention relates to a method of selecting subjects for radical prostatectomy or non-invasive therapeutic treatment stratified by the level of expression of villin in cells of their prostate tissue samples, wherein said level of expression is determined immunochemically in vitro. Information about the level of expression of villin, e.g. absence or presence of villin in a prostate sample, helps to identify the tumor type, e.g. being or metastatic, i.e. cancer, type of cancer, grade of the disease and, thus, helps to decide how to treat the patient.

The methods of determining expression of villin of the invention may be performed manually or may comprise one or more automatic steps.

The invention also relates to use of villin as a member of a prostate cancer biomarker panel, wherein said panel comprises villin and at least one of the following proteins: prostate specific antigen (PSA), prostate specific acid phosphatase (PSAP), p63, alpha-methylacyl-coenzyme-A recemase (AMACR), P504S, cytokeratin 5/6 (CK5/6), high-molecular-weight cytokeratin 34 beta E12 (34bE-12), chromogranin, CDX-2, cytokeratin 7 (CK7), and cytokeratin 20 (CK20). In one embodiment the panel comprises at least three biomarkers, wherein the first biomarker is villin and second is PSA. In one embodiment the panel comprises at least four prostate cancer biomarkers including villin, PSA, PSAP and AMACR. In one embodiment the panel comprises at least five prostate cancer biomarker including villin, PSA, PSAP, AMACP and P504S.

Basal cell-associated markers p63, high-molecular-weight cytokeratin 34 beta E12, cytokeratin 5/6 or a cocktail containing p63 and high-molecular-weight cytokeratin 34 beta E12 or cytokeratin 5/6 and prostate carcinoma-specific marker alpha-methylacyl coenzyme A (coA) racemase alone or in combination are useful adjuncts in confirming prostatic carcinoma that either lacks diagnostic, qualitative or quantitative features or that has an unusual morphologic pattern (e.g, atrophic, pseudohyperplastic) or is in the setting of prior treatment. The combination of alpha-methylacyl coA racemase positivity with negative staining for basal cell-associated markers supports a malignant diagnosis in the appropriate morphologic context. Dual chromogen basal cell-associated markers (p63 [nuclear] and high-molecular-weight cytokeratin 34 beta E12/cytokeratin 5/6 [cytoplasmic]) and alpha-methylacyl coA racemase in an antibody cocktail provide greater sensitivity for the basal cell layer, easing evaluation and minimizing loss of representation of the focal area interest because the staining is performed on one slide. In the posttreatment setting, pancytokeratin facilitates detection of subtle-treated cancer cells. Prostate-specific antigen and prostatic acid phosphatase markers are helpful in excluding secondary malignancies involving the prostate, such as urothelial carcinoma, and occasionally in excluding nonprostatic benign mimickers, such as nephrogenic adenoma, mesonephric gland hyperplasia, and Cowper glands. Accordingly, a panel of biomarkers for identification of prostate cancer comprising villin may very advantageous in cancer diagnostics, and in particular in prostate cancer diagnostics e.g. for differentiating primary and metastatic prostate tumors, for distinguishing between malignant and benign prostate tumors, for determining the grade and/or variant of prostate cancer, etc. Accordingly, in ne embodiment, the invention relates to a method of stratifying prostate cancer subjects by type and/or tumor variant.

Another aspect of the invention relates to diagnostic kits that are useful for identifying prostate cancer in a subject and/or determining the prostate cancer variant and/or grade by determining the level of expression of villin and, optionally, the level of expression of other protein biomarker(s) of prostate cancer, and, optionally, the level of expression of protein biomarker(s) of normal prostate cells or benign prostate tumor i.e. non-cancerous, cells. The kits of the invention comprise at least one antibody to villin and optionally at least one antibody to any of the following proteins: PSA, PSAP, AMACR, p63, P504S, CK5/6, 34bE-12, chromogranin, CDX-2, CK7, and CK20. In one embodiment, the kit comprises an anti-villin, PSA and CDX-2 or CK20 antibodies. In another embodiment the kit comprises an anti-villin, PSAP and CDX-2 or CK20. In one embodiment the kit may comprise an anti-villin, AMACR and CDX-2 or CK20. In some embodiments, the latter kits may further comprise p63 and/or P504S.

In one aspect the invention relates to determining whether a prostate tumor is metastatic or benign, comprising immunochemically determining expression of at least two prostate cancer specific biomarkers, wherein a first of the least two biomarkers is villin and a second is, optionally, PSA, PSAP or AMACR, in a sample of said tumor by using a kit comprising primary antibodies against the latter proteins.

Thus, the invention relates to a number of different kits comprising at least two different primary antibodies whereof one antibody is an antibody that is capable of specifically binding to villin. Kits of the invention may be composed of antibodies suitable for different immunological applications, e.g. IHC, immunoblotting, ELISA, etc. The kits may optionally comprise additional reagents, e.g. labeled antibodies, polymeric antibody conjugates, secondary antibodies, buffers, etc. which are useful for the purposes of the invention

EXAMPLES

The following is an illustrative non-limiting working example of the invention.

Immunohistochemical Staining of Tissue Samples of Prostate Tumors.

Equipment: Dako Autostainer plus and PT module.

Specimen: Benign prostatic hyperplasia (8 cases) and prostate adenocarcinoma (14 cases)

Reagents

1. Antibodies—Villin, CDX-2, PSA, Chromogranin-A, CK7, CK20, CK5/6, HMWCK (34βE12), and P504s (all from Dako); Villin (clone CWWB1, Vector Laboratoies, Inc., CA).

2. Antigen retrieval solution (Dako, Cat. No. S2367); Antibody diluent (Dako, Cat. No. S0809), Peroxidase blocking reagent (Dako, Cat. No. S2001); Dual endogenous enzyme block (Dako, Cat. No. 2009).

IHC Protocol:

Antigen Retrieval in PT module 15 min at 65 to 97° C. (warm up time)

20 min at 97° C.

20 min cooling to 82° C.

15 min cooling to 65° C.

Autostainer Plus Protocol:

Peroxidase block 5 minutes
Primary antibody 20 minutes
Visualization system—FLEX 20 minutes
Chromogen DAB+ 10 minutes
Hematoxylin 5 min Experiment Design: The 14 cases of prostate adenocarcinoma and 8 benign prostatic hyperplasia (BPH) samples of the study were selected from the Dako's internal tissue bank. Tissue sections were subjected to Dako's Target Retrieval Solution at 97° C. in a PT Link Module and IHC analysis was performed using Dako RTU and cocktailed antibodies on Dako Autostainer Plus instrument. Immunohistochemical testing using villin, chromogranin A and cocktail of 34βE12, CK5/6, and P504S antibodies was conducted in all 22 cases. For all villin positive cases, a differential panel of biomarkers consisting of PSA, CDX-2, CK7, and CK20 was then used to determine whether the neoplastic cells were of metastatic colonic adenocarcinoma or prostatic origin.

Results: Positive villin staining (clone 1D2 C3, Dako Cat. No. 3637) was observed in all tumor cells from prostate adenocarcinoma. These tumor cells also showed positive immunostaining for PSA and P504S, but they were negative for CDX-2, CK7, CK20, 34βE12, CK5/6 and chromogranin A. A few positive villin cells were also observed in normal and hyperplastic gland area in 3 (out of 8) BPH cases.

IHC staining using another villin antibody (clone CWWB1, Vector Laboratories) was also positive for villin in the prostate cancer samples used in this study. Results of IHC staining for villin, CDX-2 and PSA are demonstrated on FIG. 1.

Discussion and Conclusion: Villin is expressed by prostate adenocarcinoma. The positive PSA staining in villin stained cells confirms prostate origin of the villin stained tumor cells and rules out that the cells are of metastatic colon carcinoma origin; this being also confirmed by the negative staining for CDX-2 and CK20. The status of expression of villin in prostate cancer may be use for stratifying prostate cancer subjects into villin positive and negative groups for diagnostic or therapeutic purpose.

The invention claimed is:

1. A method of immunohistochemical characterization of solid tissue samples of prostate, comprising one or more prostate tumor cells, comprising:
   (i) providing a sample obtained from the solid tissue of prostate obtained from a subject;
   (ii) contacting the sample with a monoclonal anti-villin antibody;
   (iii) detecting in the sample, the one or more prostate tumor cells comprising the anti-villin antibody bound to villin protein; and
   (iv) immunohistochemically characterizing the sample, wherein the anti-villin antibody binds to villin protein expressed in the prostate tumor cells.

2. The method of claim 1, wherein the method further comprises detecting the bound villin antibody.

3. The method of claim 1, wherein the sample is a biopsy specimen.

4. The method of claim 1, further comprising contacting the sample with one or more additional antibodies which bind to one or more of prostate specific antigen (PSA), prostate specific acid phosphatase (PSAP), p63, alpha-methylacyl-coenzyme-A racemase (AMACR), P504 S, cytokeratin 5/6 (CK5/6), high-molecular-weight cytokeratin 34 beta E12 (34 bE-12), chromogranin, CDX-2, cytokeratin 7 (CK7), and cytokeratin 20 (CK20).

5. The method of claim 4, wherein the one or more additional antibodies bind to one or more of PSA, PSAP, and AMACR.

6. The method of claim 5, further comprising contacting the sample with an antibody which binds to CDX-2.

* * * * *